(12) United States Patent
    Calhoun et al.

(10) Patent No.: US 12,642,695 B2
(45) Date of Patent: Jun. 2, 2026

(54) ILLUMINATING EYE DEPRESSOR

(71) Applicant: Alcon Inc., Fribourg (CH)

(72) Inventors: Michael W. Calhoun, Lighthouse Point, FL (US); Gary Ganiban, Merritt Island, FL (US); Paul R. Hallen, Colleyville, TX (US); Patrick John Sadd, Colleyville, TX (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 18/636,685

(22) Filed: Apr. 16, 2024

(65) Prior Publication Data

US 2024/0350308 A1     Oct. 24, 2024

Related U.S. Application Data

(60) Provisional application No. 63/496,989, filed on Apr. 19, 2023.

(51) Int. Cl.
    *A61F 9/007*     (2006.01)
    *A61B 90/30*     (2016.01)
    *A61B 90/35*     (2016.01)

(52) U.S. Cl.
    CPC .......... *A61F 9/00736* (2013.01); *A61B 90/35* (2016.02); *A61B 2090/306* (2016.02)

(58) Field of Classification Search
    CPC ........... A61B 17/0231; A61B 2090/306; A61F 9/00736
    USPC .................................................. 600/201–246
    See application file for complete search history.

(56) References Cited

U.S. PATENT DOCUMENTS

| | | | |
|---|---|---|---|
| 4,299,227 A | 11/1981 | Lincoff | |
| 5,671,508 A | 9/1997 | Murai | |
| 6,083,155 A | 7/2000 | Trese | |
| 6,440,065 B1 | 8/2002 | Hered | |
| 6,702,237 B2 | 3/2004 | Rubenstein | |
| 6,856,505 B1 | 2/2005 | Venegas | |
| 7,258,583 B1 | 8/2007 | Baiza | |
| 7,419,493 B2 | 9/2008 | Olsen | |
| 7,910,829 B2 | 3/2011 | Sculler | |
| 8,235,893 B2 | 8/2012 | Josephberg | |

(Continued)

FOREIGN PATENT DOCUMENTS

| | | | |
|---|---|---|---|
| EP | 3738558 A1 * | 11/2020 | ............. A61B 90/30 |
| EP | 3793047 A1 | 3/2021 | |

(Continued)

OTHER PUBLICATIONS

Ganiban, et al., U.S. Appl. No. 62/114,848, "Devices and Methods to Provide Hands Free Scleral Depression During Ophthalmic Procedures," filed Feb. 11, 2025, 43 pgs.

(Continued)

*Primary Examiner* — Eduardo C Robert
*Assistant Examiner* — Tara Rose E Carter
(74) *Attorney, Agent, or Firm* — Patterson + Sheridan, LLP

(57) ABSTRACT

An eye depressor with a light for directing through a sclera. The depressor may removably accommodate a light instrument that might be used to illuminate an area in an eye during an eye surgery. The coupling of the light instrument to the depressor during the procedure may reduce the number of hands required in carrying out the surgery. This may be of particular benefit for eye surgery where limited surgical space is available.

14 Claims, 7 Drawing Sheets

(56) References Cited

U.S. PATENT DOCUMENTS

| | | | |
|---|---|---|---|
| 10,050,423 | B1 | 8/2018 | Meyer |
| 10,238,285 | B2 | 3/2019 | Farley et al. |
| 10,251,634 | B2 | 4/2019 | Foxman |
| 10,470,651 | B2 | 11/2019 | Vijfvinkel |
| 10,898,371 | B2 | 1/2021 | Olson |
| 11,166,708 | B2 | 11/2021 | Charles |
| 11,258,240 | B1 | 2/2022 | White |
| 11,266,395 | B2 | 3/2022 | Ganiban |
| 11,419,695 | B2 | 8/2022 | Kehren-quitsdorf |
| 11,826,033 | B2 | 11/2023 | Easley |
| 11,876,363 | B2 | 1/2024 | Moore |
| 2003/0139808 | A1 | 7/2003 | Shahinpoor |
| 2004/0204727 | A1 | 10/2004 | Olsen |
| 2008/0243139 | A1 | 10/2008 | Dusek |
| 2010/0004499 | A1 | 1/2010 | Brigatti |
| 2011/0021882 | A1 | 1/2011 | Selover |
| 2013/0072749 | A1* | 3/2013 | Fairneny ............ A61B 17/4241 600/37 |
| 2015/0359529 | A1* | 12/2015 | Ganiban ............ A61B 17/0231 600/203 |
| 2017/0172692 | A1* | 6/2017 | Mirsepassi ............ A61B 90/36 |
| 2020/0360104 | A1 | 11/2020 | Kehren-quitsdorf |
| 2023/0040005 | A1 | 2/2023 | Charles |
| 2023/0084104 | A1 | 3/2023 | Easley |
| 2025/0057694 | A1 | 2/2025 | Ganiban et al. |

FOREIGN PATENT DOCUMENTS

| | | |
|---|---|---|
| KR | 20170009451 A | 1/2017 |
| WO | 9302624 A1 | 2/1993 |
| WO | 2004054487 A2 | 7/2004 |
| WO | 2014071054 A1 | 5/2014 |
| WO | 2015195748 A2 | 12/2015 |
| WO | 2024008662 A1 | 1/2024 |

OTHER PUBLICATIONS

Ganiban, et al., U.S. Appl. No. 62/013,326, "Devices and Methods to Provide Hands Free Scleral Depression During Ophthalmic Procedures," filed Jun. 17, 2014, 33 pgs.
Ganiban, et al.,U.S. Appl. No. 62/042,549, "Devices and Methods to Provide Hands Free Scleral Depression During Ophthalmic Procedures," filed Aug. 27, 2014, 43 pgs.

* cited by examiner

ILLUMINATING EYE DEPRESSOR

DESCRIPTION OF THE RELATED ART

Over the years, many dramatic advancements in the field of eye surgery have taken place. Regardless of the particular procedure, several types of tools are generally employed. For example, an interventional tool that is tasked with directly engaging with and affecting a part of the eye may be utilized. A common example of such a tool is a vitrectomy probe utilized in a vitrectomy. A vitrectomy is the removal of some or all of the vitreous humor from a patient's eye. In some cases, where the surgery was limited to removal of clouded vitreous humor, the vitrectomy may constitute the majority of the procedure. However, a vitrectomy may accompany cataract surgery, surgery to repair a retina, to address a macular pucker or a host of other issues.

In support of a vitrectomy or other interventional procedure as described above, the eye may be illuminated. Thus, visualization, directly or through a microscope, may be enhanced for the surgeon that is performing the interventional procedure. This is often achieved through the use of a chandelier which is a simple, fairly uniform light instrument. In both cases, the vitrectomy probe needle and the main body of the chandelier, are each inserted through a pre-placed cannula at the surface of the eye. Each cannula provides a structurally supportive conduit strategically located at an offset location at the front of the eye, such as the pars plana. In this way, the probe needle or the chandelier may be guidingly inserted into the eye in a manner that avoids damage to the patient's lens or cornea.

Of course, in order to achieve a successful vitrectomy or other such intervention, some additional tools may be required. In some circumstances, this may include utilizing a depressor. A depressor is an instrument that is configured to intentionally and temporarily impart a scleral indentation at an offset eye location. The idea is generally to help the surgeon to forcibly manipulate the position of the eye. So, for example, the surgeon may wish to address an issue at the periphery of the eye that, in absence of some degree of manipulation, there may not be adequate access to address. By the same token, manipulating the eye with a depressor may be done as a matter of inspection more so than to position the eye to address a known issue. Indeed, in many circumstances, small injuries or surface issues are made apparent simply by introducing the depressor to the eye, even before any repositioning or further manipulating of the eye occurs. In this sense, the depressor may often be employed as a quality control instrument to aid the surgeon in evaluating the eye following a procedure such as the noted vitrectomy.

As indicated above, much like the cannula placement, the depressor interfaces the eye at offset scleral locations. Specifically, the depressor may be wedged between the fornix of the eye and the sclera at various circumferential locations as the eye is examined or positioned to address any further issues. In order to attain a full picture of the condition of the eye as aided by the depressor, this will include pressing the depressor against the sclera near the fornix and repeating this maneuver repeatedly, perhaps 10 to 20 times or more, as the depressor is positioned and re-positioned clockwise or counter-clockwise around the eye.

In addition, recall that in the example vitrectomy described above, the depressor may be introduced near the end of the procedure as a matter of inspection and quality control or to aid in positioning of the eye to address peripheral issues. Regardless, this means that a light instrument and the vitrectomy probe are already on the premises. However, the surgeon only has two hands. Furthermore, the limited geography of such eye procedures means that allowing any hand other than the surgeon's in the space around the eye is generally difficult. Thus, the surgeon is often left with the option of temporarily removing one of the light or vitrectomy instruments, awkwardly introducing another surgeon's arm into the region or taking some other undesirable step. Therefore, as a practical matter, for conventional procedures, the ability to take full advantage of the illuminating tool, the interventional tool and the depressor all at the same time is compromised.

SUMMARY

A depressor for manipulating an eye during a surgical procedure. The depressor includes a handle with an inner channel. A light source may be coupled to the handle (e.g., a chandelier or a fiber optic may be attached to a distal end of the handle or a chandelier or a fiber optic may be attached directly to a head of the depressor). In some embodiments, the light source is coupled to the distal end of the depressor and the light is directed through the inner channel to a window in the head of the depressor. In some embodiments, the chandelier or fiber optic is attached directly to the head to provide light to the window (in some embodiments, a cable to the chandelier/fiber optic may be secured in a channel along the body of the handle). The window may be a transparent or semi-transparent window located at an arcuate face in the head of the depressor.

DETAILED DESCRIPTION

In the following description, numerous details are set forth to provide an understanding of the present disclosure. However, it will be understood by those skilled in the art that the embodiments described may be practiced without these particular details. Further, numerous variations or modifications may be employed which remain contemplated by the embodiments as specifically described.

Embodiments are described with reference to certain types of vitrectomy probe surgical procedures. In particular, a procedure in which vitreous humor is removed to address vitreous hemorrhage is illustrated. However, tools and techniques detailed herein may be employed in a variety of other manners. Specifically, embodiments of illuminating scleral depressors may be utilized to facilitate tools such as a vitrectomy probe in addressing retinal detachments, macular pucker, macular holes, vitreous floaters, diabetic retinopathy or a variety of other eye conditions. Similarly, such depressors may be utilized in facilitating evaluation of the eye following such procedures. Regardless, so long as the surgical procedure is aided by the use of a scleral depressor with built-in illuminating capacity, appreciable benefit may be realized.

Figure 1:
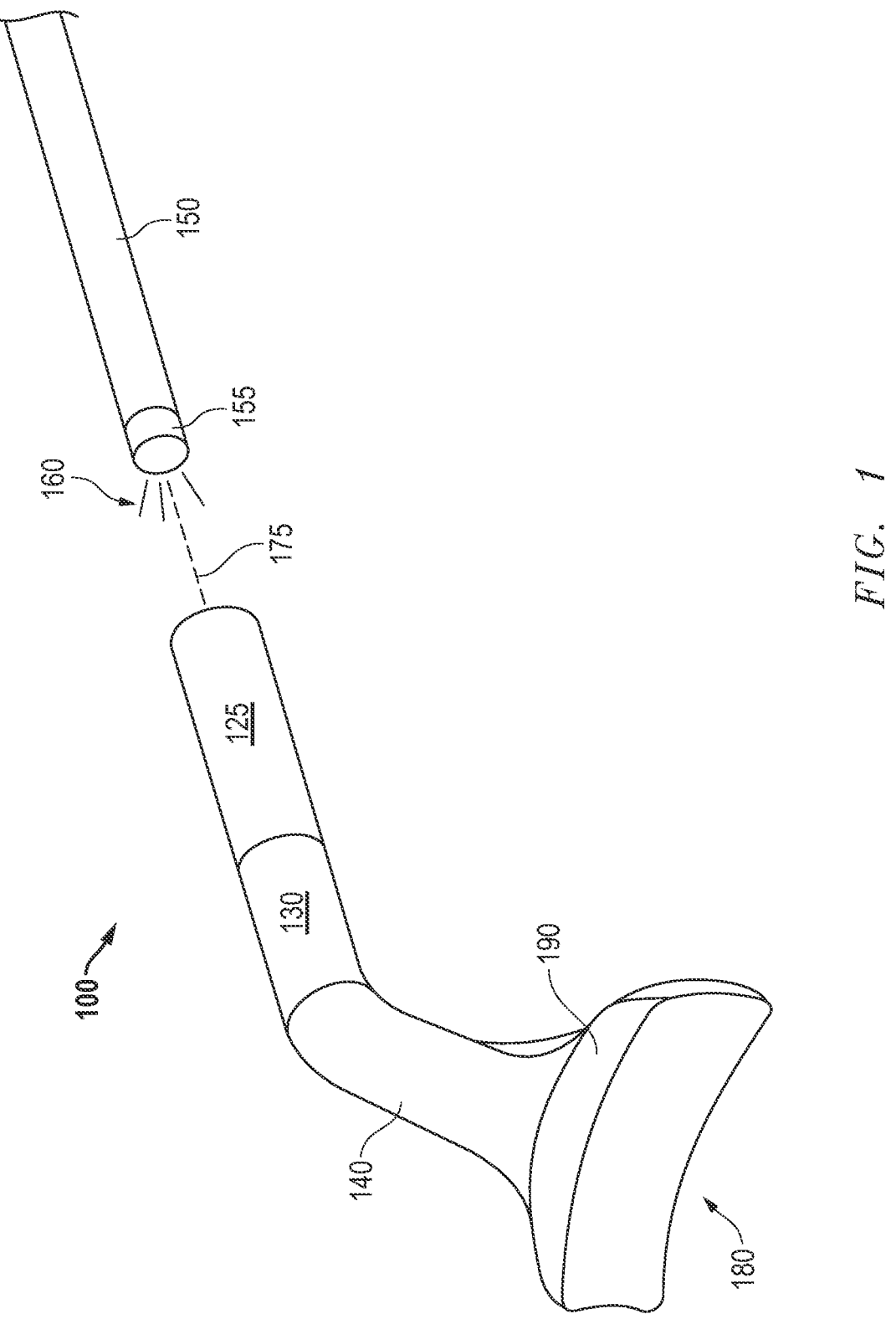
FIG. 1 is an exploded perspective view of an embodiment of an illuminating scleral depressor accommodating a light instrument.

Referring now to FIG. 1, an exploded perspective view of an embodiment of an illuminating scleral depressor 100 accommodating a light instrument 150 is shown. The instrument 150 includes a light source 155 for emitting light 160 as illustrated. Along these lines, the light instrument 150 may be a conventional chandelier employing a conventional light emitting diode (LED) source or other type of readily available instrument 150 commonly utilized in surgical eye procedures. For example, instrument 150 could be an endo-illuminator or other fiber optic interface. That is, for the embodiment illustrated, there is no requirement for modifications to a conventional light instrument 150 in order to be utilized as described herein. Of course, other depressor embodiments utilizing light sources outside of a chandelier light instrument 150 may be utilized (e.g. see FIG. 3). Further, in some embodiments, a specialized chandelier (i.e., non-conventional) designed to interface with the depressor 100 may be used.

Continuing with reference to FIG. 1, the instrument 150 may be received by the depressor 100 along a central axis 175. Specifically, for the embodiment shown, a tubular housing that includes a coupling segment 125 and a channelizing segment 130 is illustrated. Alternatively, the housing may be considered to be a singular monolithic tubular piece. With added reference to FIG. 2, the segmenting of the housing reflects the fact that for the embodiment illustrated, a coupling mechanism 200 is provided at the rear of the housing corresponding to the noted coupling segment 125 to secure the light instrument 150. In one embodiment, the linear housing of the coupling 125 and channelizing 130 segments are cumulatively between about 2.5 and 3.5 inches in length with the coupled instrument 150 reaching between about 0.25 to 0.75 inches into the interior and stably secured thereat. Other dimensions are also contemplated.

At the other end of the housing relative the light instrument 150 is a transition segment 140 of the depressor 100. Again, the housing may be thought of as a unitary tubular piece. However, in the embodiment shown, the transition segment 140 is highlighted separately in that it constitutes a portion of the housing that angles away from the central axis 175. Furthermore, as discussed below, this segment 140 may be of a stable but malleable material such as a platinum. This allows the surgeon to shape or bend the segment at a patient's fornix 350 for potential hands-free placement of the depressor 100 (see FIG. 3).

Figure 5:
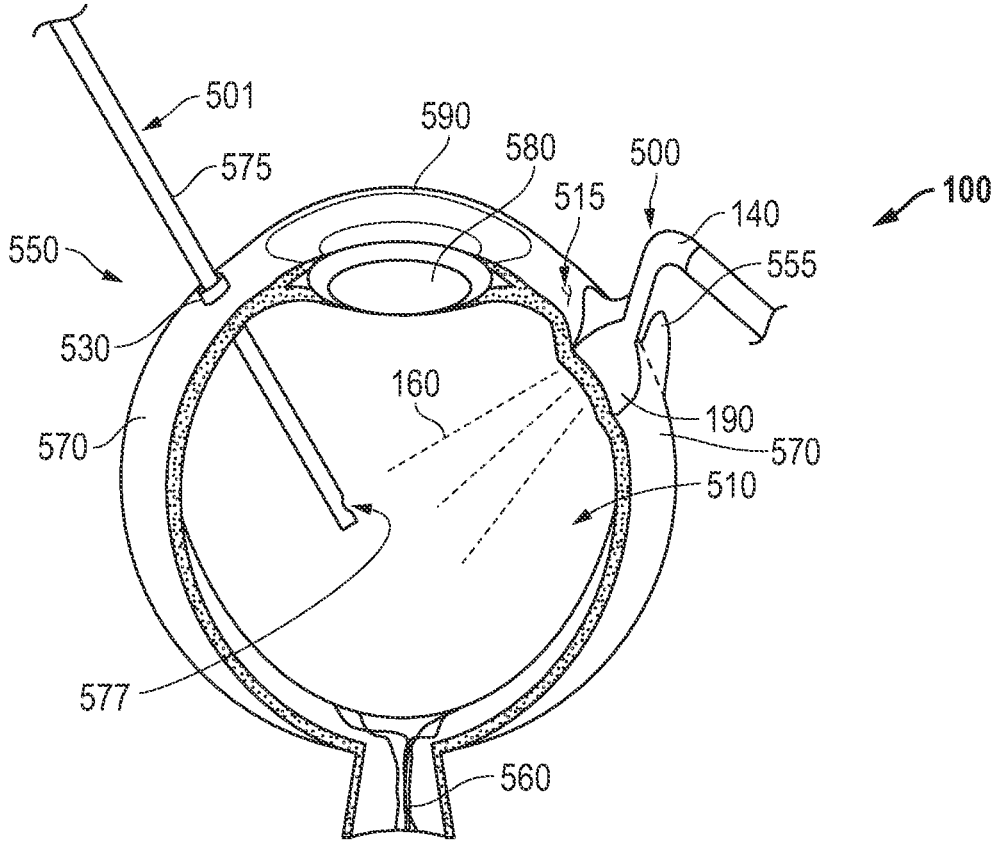
FIG. 5 is a perspective overview of an illuminating scleral depressor utilized in supporting an eye surgery.

With added reference to FIG. 5, the depressor 100 is outfitted with a head 190 that includes a face 180 for interfacing an eye 550 in order to impart a depressor function at an outer surface of the sclera 570 as described herein. In one embodiment where the head 190 is not entirely transparent, the face 180 will still include a window to allow light 160 that passes from the light instrument 150 and through the housing segments 125, 130, 140 to emerge. In one embodiment, the window is of an amorphous thermoplastic molding compound for enhanced clarity. In another embodiment the substantial entirety of the head 390 may be of such transparent materials (e.g., see FIG. 3). Regardless, with the depressor 100 in position as illustrated in FIG. 5, this may facilitate the distribution of light 160 into an interior of the eye 550 as an aid to a surgical procedure therein. Such illumination may be beneficial for the illustrated vitrectomy, to address retina breaks, to support a vitreous base dissection or for any number of other procedures.

Figure 2:
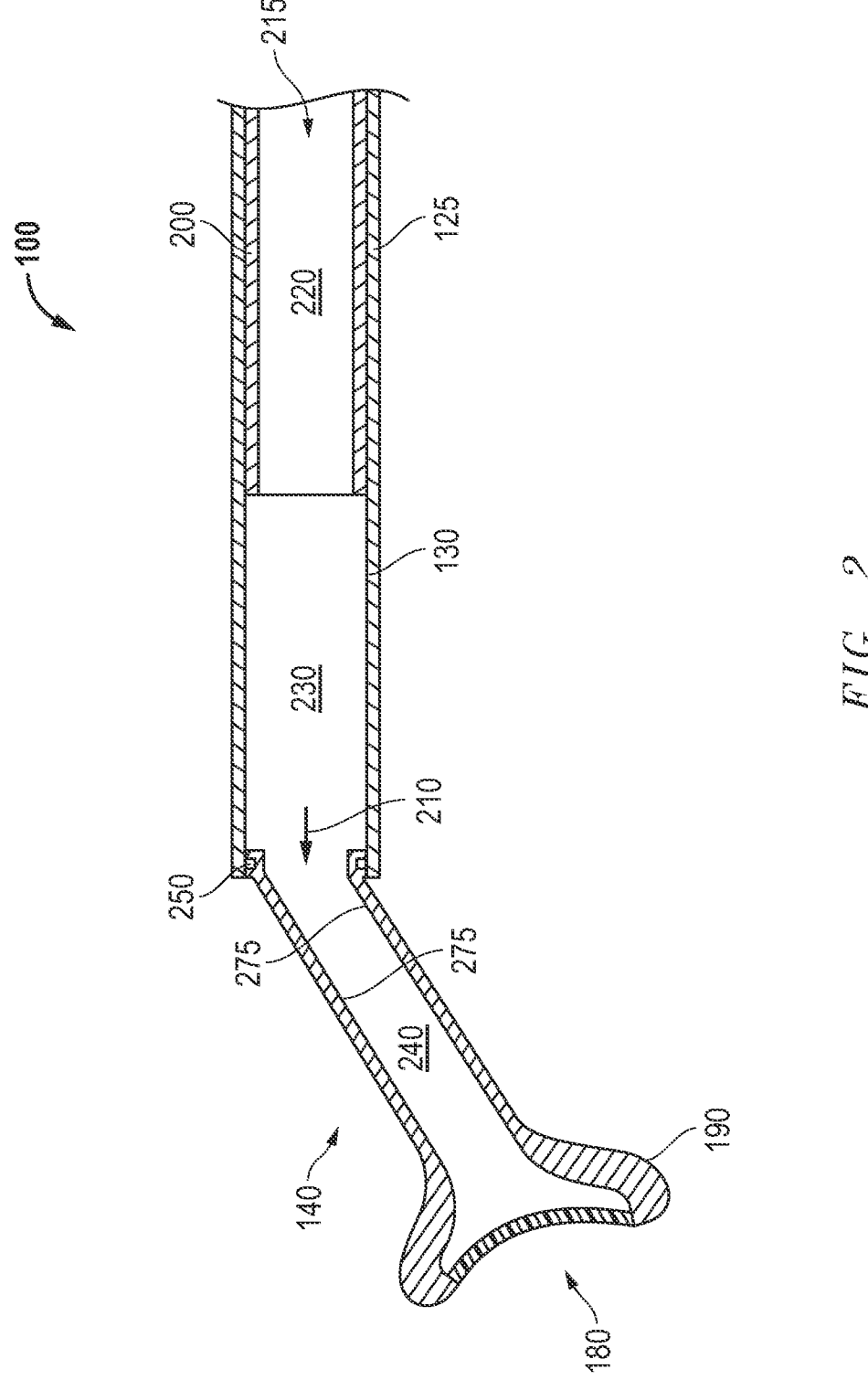
FIG. 2 is a side cross-sectional view of the scleral depressor of FIG. 1 illustrating an internal channel.

Referring now to FIG. 2, with added reference to FIG. 1, a side cross-sectional view of the scleral depressor 100 is shown illustrating an internal channel 215. For this embodiment, the channel 215 includes a coupling region 220, a collimating region 230 and a transitional region 240. As alluded to above, the coupling region 220 accommodates a coupling mechanism 200. This mechanism 200 may consist of a tubular insert immobily secured within the distal end of the channel 215 for sake of reducing the channel diameter to tightly accommodate the light instrument 150 of FIG. 1. That is, a simple frictional force fit, or interference fit, of the instrument 150 by the mechanism 200 may be sufficient to stably secure the instrument 150 in place for an eye surgery as detailed further below. Of course, in other embodiments, the mechanism 200 may be of a more complex design such as being of a compressible material for a tightened fit or including a keyed or locking feature to match with a corresponding feature of the instrument 150. Further, the mechanism 200 may not be a separate insert as illustrated. Rather the diameter of the coupling segment 125 may simply be small enough to tightly secure the instrument 150 or outfitted with keying features or other mode of securing the instrument 150 for a procedure as suggested above.

Continuing with reference to FIG. 2, for the embodiment illustrated the channel 215 includes a collimating region 230. It is not a requirement that this region 230 be a part of the channel 215. In some embodiments, the light source 155 of FIG. 1 may emerge directly at the transitional region 240 of the channel 215 when the light instrument 150 is plugged into the coupling region 220. In other embodiments, a degree of distance (e.g., the collimating region 230), may be present. As noted above, the instrument 150 of FIG. 1 may reach no more than between about 0.25 and 0.75 inches into the distal end of the depressor 100. In some embodiments, this arrangement may keep the light source 155 from physically interfacing the internal structure of the transition segment 140, and allow for the structure of the channelizing segment 130 to perform a collimating function. That is, the light path 210 for light 160 from the light source 155 of FIG. 1 may be channelized or collimated by travelling along the collimating region 230 before reaching the transitional segment 240. Thus, the light ultimately reaching the face 180 may be maximized. In one embodiment, the channelizing segment 130 is a metal with the inner surface defining the collimating region 230 being polished to further enhance the amount of light reaching the face 180.

Continuing with reference to FIG. 2, the channel 215 of the depressor 100 ends in the transitional region 240 as defined by the transition segment 140, ultimately leading to a face 180 as described above. In the embodiment shown, this segment 140 is separately secured by a snap-fit ring 250. However, any number of different attachment features may be employed (e.g., friction fit, adhesive, etc.) Regardless, in some embodiments, the discretely separate nature of the transition segment 140 is due to the fact that it is angled away from the axis 175 as illustrated in FIG. 1 and due to the malleable nature of the segment 140. Both of these aspects of the transition segment 140 are discussed further below with respect to utilizing the depressor 100 to support an eye surgery.

In some embodiments, a malleable biocompatible metal such as platinum, titanium or a suitable alloy may be used for the transition segment 140. Further, as with the channelizing segment 130, the internal surface 275 may be a polished metal to help avoid light absorption and ensure that the change in direction of the light path 210 into the transitional region 240 is supported, again enhancing the light reaching the face 180. Other materials may also be used for the transition segment 140 (e.g., plastic).

Figure 3:
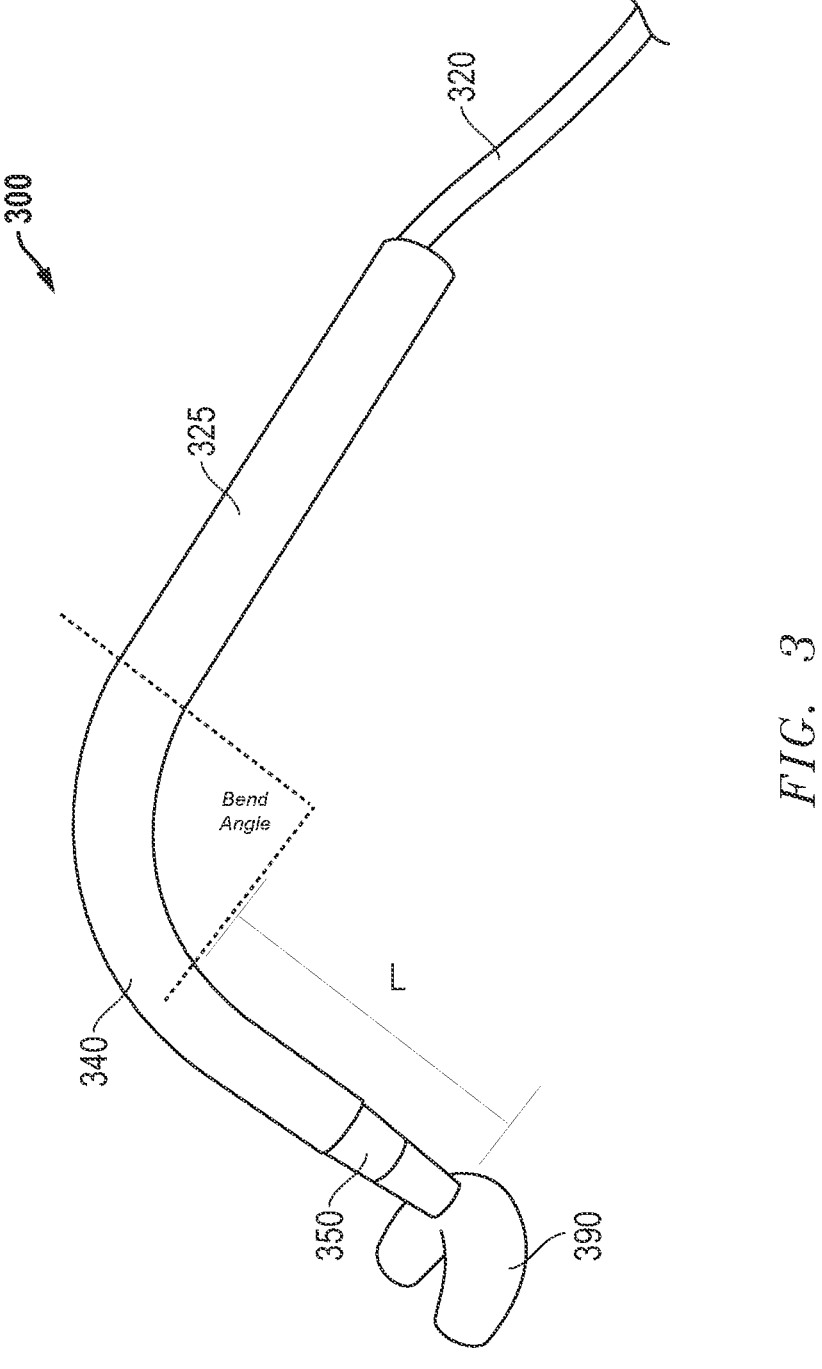
FIG. 3 is a side perspective view of an alternate embodiment of an illuminating scleral depressor.

Referring now to FIG. 3, a side perspective view of an alternate embodiment of an illuminating scleral depressor 300 is shown. In this embodiment, the substantial entirety of the head 390 is of a unitary form constructed of a transparent material such as an amorphous thermoplastic molding compound for enhanced clarity.

Figure 4A:
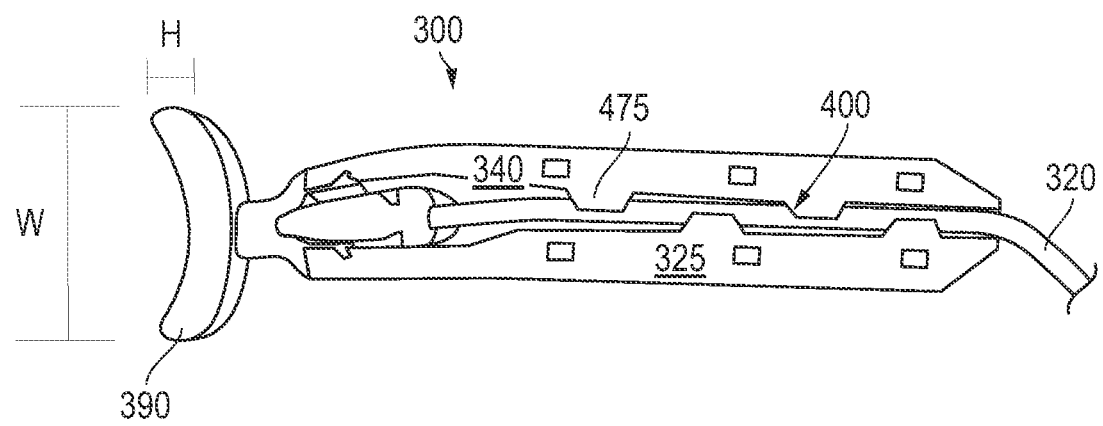
FIG. 4A is a perspective view of an underside of the illuminating scleral depressor of FIG. 3.
Figure 4B:
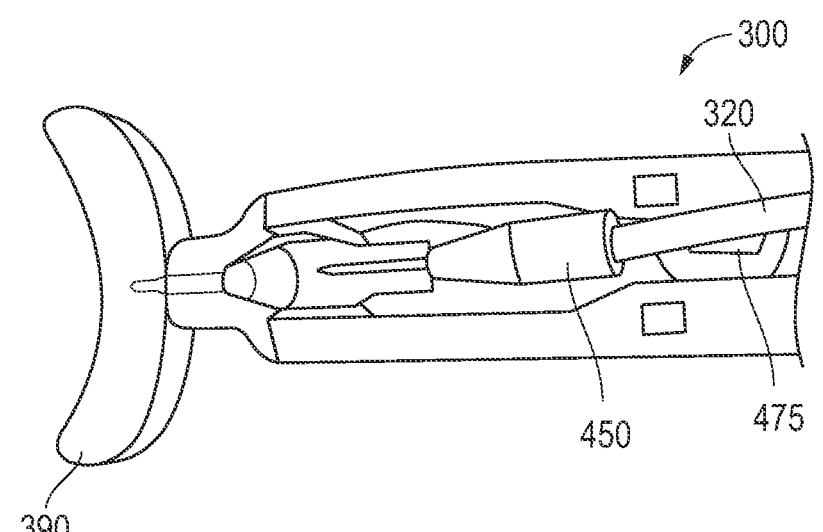
FIG. 4B is an enlarged view of an illuminating scleral depressor of FIG. 3 accommodating a light device.

In some embodiments, the light source for the embodiment of FIG. 3 is a chandelier or a fiber optic line 320 that runs the length of the body 325, transition segment 340 and coupling 350 as illustrated from the underside (see FIGS. 4A and 4B). Thus, fiber optic light is provided directly to the head 390 without any need for channelizing or collimating light to the head 390. This may be of substantial benefit for embodiments where the transition segment 340 is to be manipulated or shaped to any substantial degree to support a surgical procedure as illustrated in FIG. 5. That is, regardless of the amount of shaping of the transition segment 340, the line 320 reaches the head 390 without concern over how to collimate or channelize the light.

In some embodiments, the body 325 may have a bend located a length (L) from a distal end of the head 390. In some embodiments, the length (L) may be approximately in a range of 10 to 30 millimeters (mm). In some embodiments, the length (L) of the head 390 may be approximately in a range of 15 to 25 mm (e.g., 20 mm). In some embodiments, the body 325 may be flexible to allow a range of Bend Angles (e.g., from straight (0 degrees) to a right angle (90 degrees) as shown in FIG. 3). For example, the Bend Angle may be approximately in a range of 20 degrees to 70 degrees (e.g., 38.86 degrees or 51.14 degrees). In some embodiments, for example as seen in FIG. 5, the Bend Angle may be even greater than 90 degrees. In some embodiments, the Bend Angle may be fixed (e.g., if the body 325 is made of a rigid material).

Referring now to FIG. 4A, a perspective view of an underside of the illuminating scleral depressor 300 of FIG. 3 is shown. In this view, the fiber optic line 320 can be seen inserted and secured within a channel 400 running through the body 325 and transition segment 340 eventually reaching the head 390. In some embodiments, the inner channel 400 is defined by alternating tabs 475 of the housing that are configured to secure a fiber optic line, attached to the light device, (for example, a fiber optic line attached to a chandelier) along a housing from a proximal end opposite the head 390, through the housing, and to the head 390. Alternating tabs 475 of the body 325 are used to help ensure security of the line 320 in the channel 400 therebelow. Other mechanisms for securing the fiber optic line in the channel are also contemplated (e.g., a friction fit, adhesive, etc).

In one embodiment, the head 390 is tapered at the ends to facilitate initial placement at the eye 550 as shown in FIG. 5. Additionally, in some embodiments, the head 390 is secured to the coupling 350 with a gate feature that also presents a connection point for a frame to supply surrounding support for the positioning of the body 325 and transition segment 340. Various dimensions may be used for the head 390 as needed to fit different eye sizes and shapes. For example, in some embodiments, the width (W) of the head 390 may be approximately in a range of 10 to 30 mm. In some embodiments, the width (W) of the head 390 may be approximately in a range of 15 to 25 mm (e.g., 20.85 mm). As a further example, in some embodiments, the height (H) of the head 390 may be approximately in a range of 2 to 8 mm (e.g., 5 mm). In some embodiments, a cross section of a main body of the head 390 (taken in the direction of the height of the head) may be circular with a diameter that approximates the height (H) of the head 390 (e.g., a diameter approximately in a range of 2 to 8 mm (e.g., 5 mm)). As noted above, the head 390 may taper toward the ends such that the diameter also tapers towards the ends (and may become non-circular, for example, may flatten as shown in FIG. 4A). Other dimensions and cross-sectional configurations are also contemplated. In some embodiments, the depressor 300 may have similar Bend Angles as provided above for FIG. 3 at a similar depth (D) range as provided above for FIG. 3.

Referring now to FIG. 4B, an enlarged view of the illuminating scleral depressor 300 of FIG. 3 is shown accommodating the fiber optic line 320. More specifically, the line 320 is shown secured to an adapter 450 immediately prior to plugging into the head 390. The adapter 450 force fit secures the end of the line 320 by way of a size adjustable passage 410 therethrough (see FIG. 4C). In this way, the line 320 may be of varying diameters and still be accommodated by the same depressor 300. Once secured by the adapter, the adapter itself may be force fit into a matching portion of the channel 400 in order to plug the illuminating fiber optic 320 end into the transparent head 390 for use.

Figure 4C:
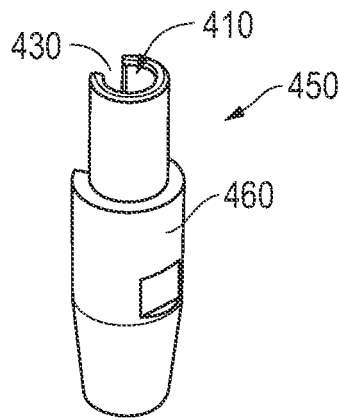
FIG. 4C is a perspective view of an embodiment of an adapter for securing the light device of FIG. 3 within the depressor of FIGS. 4A and 4B.

Referring now to FIG. 4C, a perspective view of an embodiment of the adapter 450 is illustrated in isolation. In this view, a slit 430 is illustrated which facilitates the size adjustability of the passage 410. For example, in one embodiment, the adapter 450 is a unitary form 460 of a biocompatible polymer that allows for expansion of the passage 410 at the slit 430 to accommodate the line 320. Once positioned through the passage 410, the unitary form 460 of the adapter 450 may naturally return to form with the slit 430 closing until the line 320 is securely immobilized in the passage 410. As an example, in some embodiments, the depressor 300 may be sized to directly receive a 25 gauge chandelier in the head 390 without the use of the adapter 450 and may be configured to receive a 27 gauge chandelier that has been inserted into the adapter to facilitate the fit between the smaller chandelier and the head 390. Other chandelier/adapter sizes are also contemplated.

Referring now to FIG. 5, a perspective overview of the scleral depressor 100 of FIG. 1 is shown being utilized in supporting an eye surgery. Of course, the depressor 300 of FIG. 3 might also be utilized in the same manner utilized as described here. Regardless, a vitrectomy needle 575 from a probe 501 is being utilized to address an eye issue such as treating a hemorrhage in a given eye region 510. This begins with the needle 575 of the probe 501 being inserted through a preplaced cannula 530 and directed toward the region 510. A suction may be applied and the port 577 of the probe 501 may be utilized for the uptake of blood from the hemorrhage and vitreous humor. Notice that the cannula 530 is positioned in an offset manner at the sclera 570. In this way, the more delicate cornea 590 and lens 580 may be avoided. By the same token, the optic nerve 560 is also quite delicate. Thus, visibility may be key to ensuring that the needle 575 does not inadvertently contact the nerve 560 or other delicate features at the back of the eye 550.

Continuing with reference to FIG. 5, with added reference to FIG. 1, the scleral depressor 100 is an illuminating device. That is, as discussed above, light 160 may be emitted from a face 180. In certain other circumstances, a light instrument 150 as illustrated in FIG. 1 might include a filter for tuning of the light to enhance visibility. However, in the embodiment of FIG. 5, the light 160 exits the face 180 and is directed through the outer surface of the sclera 570. Thus, a natural filter to the light is presented by the sclera 570. Therefore, no added measures for tuning the light 160 may be required.

The depressor 100 of FIG. 5 is illustrated with a hand-shaped angle 500 at the transition segment 140. That is, recall that this segment 140 is already somewhat angled as described above. Further, this segment 140 may be intentionally malleable in construction (although, in some embodiments, the segment 140 may be fixed). A shape of the head may allow the surgeon to wedge the head 190 of the depressor 100 between the sclera 570 and the fornix 555. As used herein, the term fornix 555 is meant to refer to the loose soft tissue folds surrounding the eye 550 in a generally circumferential manner. For FIG. 5, a singular region of such a fold is illustrated as the fornix 555. However, it is to be understood that the fornix 555 generally surrounds the eye 550. So, for example, the illustrated fornix 555 at the right side of the eye 550 might also be shown at the left or anywhere circumferentially thereabout. Regardless, wedging of the head 190 between the fornix 555 and sclera 570 may provide a degree of depression. Once more, in one embodiment, the surgeon may impart an increased hand-shaped angle 500 on the transition segment 140 such that the depressor 100 may rest hands-free in the depicted manner. In this particular situation, this means that while the depressor 100 is wedged in position the surgeon does not need to dedicate a hand to either a light instrument 150 or to the depressor 100.

As discussed below, the face 180 of the depressor 100 generally takes on an arcuate or concave shape to largely match the convex shape of the eye 550. Nevertheless, a degree of depression takes place pushing in on the sclera 570 as indicated. This may be undertaken to gain manipulative or interactive control over the eye 550 to support the procedure or as a matter post-procedure inspection, particularly at peripheral locations. For example, note the visual emergence of a minor surface injury 515 that is apparent following the wedged use of the depressor 100. This injury 515 may now be treated due to the inspection. In one embodiment, the face 180 of the depressor 100 may be sufficiently large enough horizontally that with a few circumferential wedges as described, the entire circumference of the eye 550 may be inspected in this manner. More specifically, the face 180 may occupy at least about approximately 10% to 30% (e.g., 16%) of an interface with the eye 550, for example, more than about 25%, or 90°, of interface with the eye 350. Other percentages are also contemplated.

Figures 6A, 6B, 6C:
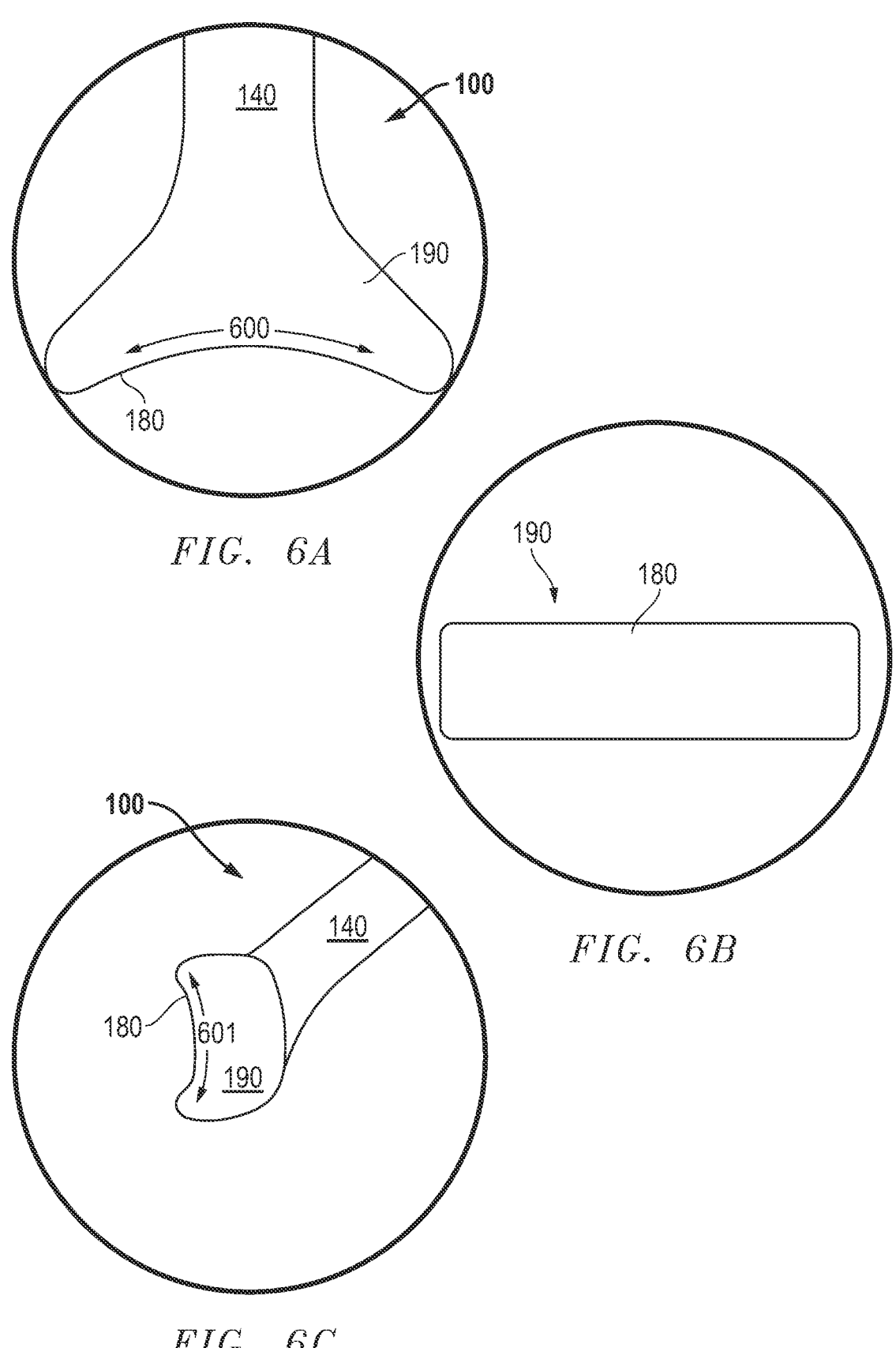
FIG. 6A is a top profile view of an illuminating scleral depressor illustrating a horizontal arcuate morphology at a face of the depressor.
FIG. 6B is a front view of the face of an illuminating scleral depressor.
FIG. 6C is a side profile view of an illuminating scleral depressor illustrating a vertical arcuate morphology at the face of the depressor.

Referring now to FIGS. 6A-6C, different views of the depressor 100 are shown with a focus on the interfacing morphology. For example, FIG. 6A is a top profile view of the illuminating scleral depressor 100 of FIG. 1 which illustrates a horizontal arcuate morphology 600 at a face 180 of the depressor 100. Of course, embodiments of a depressor 300 as illustrated in FIG. 3 may be of the same morphology. This horizontal arcuate morphology 600 is meant to largely match the corresponding convex shape of a patient's eye 550 as described above. In the embodiment shown, the morphology 600 may include the face 180 spanning a partial circumference of between about 1.5 centimeters (cm) to about 3 cm for interfacing with a 2-3 cm diameter human eye 550 as illustrated in FIG. 5. Thus, as indicated above, 16% (for example) or more of the eye 550 may be interfaced by a wedged head 190 of the transition segment 140 (again, as shown in FIG. 5).

Referring now to FIG. 6B, with added reference to FIG. 5, a front view of the face 180 of the illuminating scleral depressor 100 of FIG. 1 is shown. In this embodiment, the entirety of the face 180 may be transparent and of exceptional clarity. That is, as noted above, the light 160 passes through the sclera 570 to reach the region 510 of interest, for example. Therefore, unlike other applications where the light instrument 150 of FIG. 1 might be directly, interventionally introduced to within the eye 550, there may be no particular rationale for filtering the light 160 for the sake of enhancing visibility. Rather, this effect may be achieved by the sclera 570 itself. Of course, in some embodiments, the face may be semi-transparent.

Continuing with reference to FIG. 6B, the materials for at least the face 180 may be a biocompatible amorphous thermoplastic molding compound. Such materials are particularly well suited for injection molding during manufacture while retaining optical clarity. Of course, other materials may also be used for the face 180.

Referring now to FIG. 6C, with added reference to FIG. 5, a side "kidney bean" profile view of the illuminating scleral depressor 100 of FIG. 1 is shown illustrating a vertical arcuate morphology 601 at the face 180 of the depressor 100. Again, this concave morphology 601 is meant to interface the convex eye 550 and sclera 570 in a matching fashion. However, unlike the horizontal morphology 600 illustrated in FIG. 6A, the vertical arcuate morphology 601 is not necessarily intended to occupy any predetermined amount of eye surface. For example, use of the depressor 100 for post procedure inspection of the eye 550 may be efficiently achieved by utilizing a depressor 100 with a substantial horizontal arcuate morphology 600. However, the vertical morphology 601 does not impact this particular aspect of the use of the depressor 100. So long as the vertical morphology 601 is sufficient in size and shape to largely match the eye 550 and avoid presenting in a potentially blunt manner, the morphology 601 may be well suited for the depressor 100.

Figure 7:
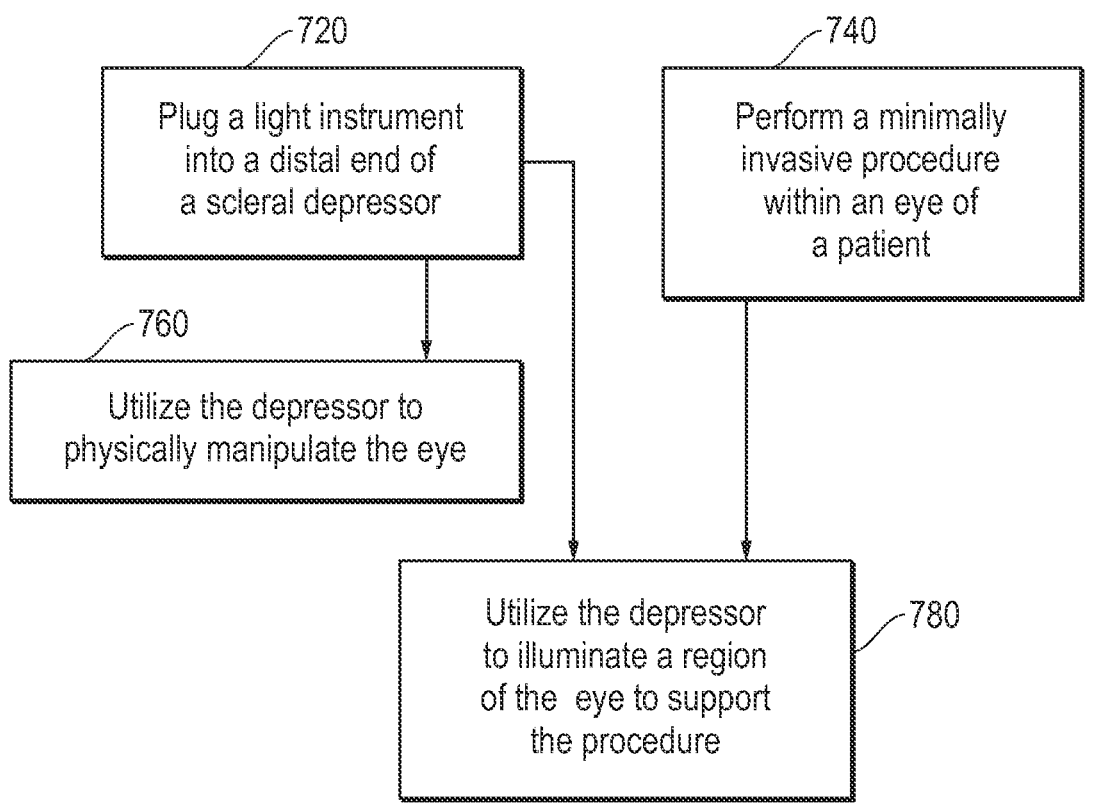
FIG. 7 is a flow-chart summarizing an embodiment of employing an illuminating scleral depressor to support an eye surgery.

Referring now to FIG. 7, a flow-chart summarizing an embodiment of employing an illuminating scleral depressor to support an eye surgery is depicted. A light instrument (which may be conventional or unique to this particular application) is plugged into the distal end of a scleral depressor as noted at 720. In some embodiments, the light instrument may be plugged directly into a head of the scleral depressor (e.g., as seen in FIGS. 4A-B. In this embodiment, a cable leading up to the chandelier or fiber optic may be secured to a handle of the depressor, for example, through tabs along a channel in the handle body (e.g., as seen in FIG. 4A). The depressor may be utilized to physically manipulate the eye (see 760). However, it may simultaneously be utilized as indicated at 780 to provide illumination to the interior of the eye through the sclera of the patient. Thus, a minimally invasive surgical procedure may also be simultaneously aided as noted at 740.

Embodiments described hereinabove include tools and techniques that support a variety of different eye surgeries with a scleral depressor that incorporates an illuminating character. This means that for procedures where a scleral depressor is introduced, illumination is not sacrificed due to the surgeon running out of hands. Furthermore, embodiments of the scleral depressor which are employed may support hands-free stable positioning. Thus, the introduction of the depressor may actually provide illumination while even further reducing the number of hands required to carry out the procedure.

The preceding description presents several embodiments and other embodiments and/or features of the embodiments disclosed but not detailed hereinabove may be employed. Furthermore, persons skilled in the art and technology to which these embodiments pertain will appreciate that still other alterations and changes in the described structures and methods of operation may be practiced without meaningfully departing from the principle and scope of these embodiments. Additionally, the foregoing description should not be read as pertaining only to the precise structures described and shown in the accompanying drawings, but rather should be read as consistent with and as support for the following claims, which are to have their fullest and fairest scope.

The invention claimed is:

1. A depressor for physically interfacing with an outer surface of an eye in support of a surgical procedure, the depressor comprising:

a housing for manipulating by a surgeon, the housing including a channel; and a head coupled to the housing with a transparent or semi-transparent portion, the head to support the interfacing, the housing to accommodate a light device at the channel to direct light to the transparent or semi-transparent portion;

wherein:

the channel is defined by alternating tabs of the housing that are configured to secure a fiber optic line, attached to the light device, along the housing from a proximal end opposite the head, through the housing, and to the head, and a distal face of the head configured to contact the eye is of a concave arcuate shape and the interfacing occupies at least a portion of the eye circumferentially.

2. The depressor of claim 1, wherein the transparent or semi-transparent portion is comprised of an amorphous thermoplastic molding material.

3. The depressor of claim 1, further comprising a transition segment of the housing to accommodate the head, the transition segment being angled away from an axis of a remainder of the housing.

4. The depressor of claim 3, wherein the transition segment is comprised of a malleable material.

5. The depressor of claim 1, wherein the light device plugs into the head through an adaptor.

6. The depressor of claim 1, wherein the light device comprises a chandelier that plugs directly into the head.

7. The depressor of claim 1, wherein the alternating tabs of the housing are configured to contact the fiber optic line.

8. The depressor of claim 1, wherein the channel extends through a sidewall of the housing.

9. A surgical instrument set for used in eye surgery, the surgical instrument set comprising: a scleral depressor with a head for interfacing with an outer surface of a sclera of an eye in support of the eye surgery and a housing to accommodate a light device to supply light to the head and for manipulating by a surgeon, the housing including a channel defined by alternating tabs of the housing that are configured to secure a fiber optic line, attached to the light device, and the head coupled to the housing with a transparent or semi-transparent portion, the head further coupled to the light device; and an invasive surgical eye instrument to perform the eye surgery, the eye surgery visibly aided by the light emerging from a face of the head at the interface with the sclera; wherein: a distal face of the head configured to contact the eye is of a concave arcuate shape and the interfacing occupies at least a portion of the eye circumferentially.

10. The surgical instrument set of claim 9, wherein the head is of a kidney bean profile with tapered ends for wedging between the sclera and a fornix of the eye during the interfacing.

11. The surgical instrument set of claim 9, wherein the light device is one of the fiber optic line terminating at the head and a chandelier, incorporating the fiber optic line, removably coupled to the housing.

12. The surgical instrument of claim 11, wherein the head is of unitary construction and substantially transparent for the terminating of the fiber optic line thereat.

13. The surgical instrument of claim 9, wherein the light device plugs into the head through an adaptor.

14. The surgical instrument of claim 9, wherein the light device comprises a chandelier that plugs directly into the head.

* * * * *